United States Patent
Yamada et al.

(10) Patent No.: US 10,323,048 B2
(45) Date of Patent: Jun. 18, 2019

(54) ORGANOSILICON COMPOUND AND PRODUCTION PROCESS THEREFOR

(71) Applicant: SHIN-ETSU CHEMICAL CO., LTD., Tokyo (JP)

(72) Inventors: Tetsuro Yamada, Annaka (JP); Munenao Hirokami, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/081,175

(22) PCT Filed: Jan. 30, 2017

(86) PCT No.: PCT/JP2017/003196
§ 371 (c)(1),
(2) Date: Aug. 30, 2018

(87) PCT Pub. No.: WO2017/154405
PCT Pub. Date: Sep. 14, 2017

(65) Prior Publication Data
US 2019/0031690 A1  Jan. 31, 2019

(30) Foreign Application Priority Data

Mar. 10, 2016  (JP) ................. 2016-047178

(51) Int. Cl.
| C07F 7/18 | (2006.01) |
| C09J 183/12 | (2006.01) |
| C09D 183/12 | (2006.01) |

(52) U.S. Cl.
CPC .......... *C07F 7/1804* (2013.01); *C09D 183/12* (2013.01); *C09J 183/12* (2013.01)

(58) Field of Classification Search
None
See application file for complete search history.

(56) References Cited

U.S. PATENT DOCUMENTS

| 4,738,892 A | 4/1988 | Canova |
| 5,336,786 A | 8/1994 | Shiobara et al. |
| 8,207,259 B2 | 6/2012 | Tsuchida |

FOREIGN PATENT DOCUMENTS

| EP | 0 179 355 A2 | 4/1986 |
| JP | 61-106585 A | 5/1986 |
| JP | 62-83342 A | 4/1987 |
| JP | 4-175306 A | 6/1992 |
| JP | 2116569 A1 | 3/1993 |
| JP | 6-172370 A | 6/1994 |
| JP | 6-505998 A | 7/1994 |
| JP | 7-82276 A | 3/1995 |
| JP | 2004-59741 A | 2/2004 |
| JP | 2005-120192 A | 5/2005 |
| JP | 2009-275015 A | 11/2009 |
| JP | 2012-184408 A | 9/2012 |

OTHER PUBLICATIONS

International Search Report, issued in PCT/JP2017/003196, dated Mar. 7, 2017.
Written Opinion of the International Searching Authority, issued in PCT/JP2017/003196, dated Mar. 7, 2017.

*Primary Examiner* — Clinton A Brooks
(74) *Attorney, Agent, or Firm* — Birch, Stewart, Kolasch & Birch, LLP

(57) ABSTRACT

An organosilicon compound represented by formula (1), which has, per alkoxysilyl group, a plurality of epoxy groups each capable of reacting with an organic resin moiety to form a bond and which hence is useful as a primer, a resin modifier, etc.

$$H\text{---}[H_2C\text{---}\underset{\underset{O}{\diagdown\!\diagup}}{C}\text{---}CH\text{---}CH_2]_a\text{---}[H_2C\text{---}\underset{R^3}{C}\text{=}CH\text{---}CH_2]_b\text{---}[CH_2\text{---}CH\text{---}$$

$$\text{---}CH_2\text{---}CH_2]_c\text{---}[CH_2\text{---}\underset{\underset{H_2C\diagup}{\overset{R^3\text{---}C}{\mid}}\diagdown O}{C}]_d\text{---}[CH_2\text{---}\underset{\underset{CH_2}{\overset{R^3\text{---}C}{\mid}}\parallel}{C}]_e\text{---}[CH_2\text{---}\underset{\underset{CH_3}{\overset{R^3\text{---}CH}{\mid}}}{C}]_f\text{---}A^1\text{---}A^2\text{---}Si\text{---}(OR^1)_m$$
$$R^2{}_{3-m}$$

(1)

(In the formula, the $R^1$ moieties each independently represent an (un)substituted $C_{1\text{-}10}$ alkyl group, etc.; the $R^2$ moieties each independently represent an (un)substituted $C_{1\text{-}10}$ alkyl group, etc.; the $R^3$ moieties each independently represent a hydrogen atom or a methyl group; $A^1$ represents a single bond, O, S, NH, or a divalent linking group containing a heteroatom; $A^2$ represents a single bond or an (un)substituted $C_{1\text{-}20}$ divalent hydrocarbon group optionally containing a heteroatom; a and c are each independently a number greater than 0; b, d, e, and f are each independently a number of 0 or greater; and m is an integer of 1 to 3. The repeating units may have been linked in any order.)

7 Claims, No Drawings

ORGANOSILICON COMPOUND AND PRODUCTION PROCESS THEREFOR

TECHNICAL FIELD

This invention relates to an organosilicon compound and a method for producing the same. More particularly, the invention relates to an organosilicon compound having a hydrolyzable silyl group and a plurality of epoxy groups on the molecule, a method for producing the organosilicon compound, coating and adhesive compositions containing the organosilicon compound, and cured articles of these compositions.

BACKGROUND ART

Silane coupling agents are compounds which have on a single molecule both a moiety that is reactive with inorganic matter and a moiety that is fully reactive with and soluble in organic matter. Because such agents act as adhesive aids at the interface between inorganic matter and organic matter, they are widely employed as composite resin modifiers.

Many silane coupling agents and siloxane oligomers that are partial hydrolytic condensates thereof are compounds having two or more alkoxysilyl groups per organic functional group, whereas only a few compounds having two or more organic functional groups per alkoxysilyl group.

As an example of the latter, Patent Document 1 discloses organic compounds containing two or more epoxy groups per alkoxysilyl group, wherein two glycidoxy groups and a trimethoxysilylpropyl group are attached to an aromatic ring.

However, the compounds of Patent Document 1 have a structure which, in terms of molecular design, makes it impossible to introduce three or more epoxy groups per alkoxysilyl group.

Patent Document 2 discloses compounds having three or more epoxy groups per alkoxysilyl group, wherein a plurality of glycidoxy groups and an alkoxysilyl group are attached to a polyglycerol skeleton or a sorbitol skeleton.

Yet, the compounds of Patent Document 2 are highly hydrophilic owing to the structure of the backbone and the nature of the plurality of urethane linkages, and therefore cannot be employed in coating and adhesive compositions where hydrophobic properties are required. Moreover, the structure of these compounds leads to marked declines in heat resistance, yellowing resistance and crack resistance.

PRIOR ART DOCUMENTS

Patent Documents

Patent Document 1: JP-A H06-172370
Patent Document 2: JP-A 2009-275015

SUMMARY OF INVENTION

Technical Problem

It is therefore an object of this invention to provide organosilicon compounds which have, per alkoxysilyl group, a plurality of epoxy groups capable of reacting with organic resin moieties to form bonds and thus are effective as, for example, primers and resin modifiers. Another object of the invention is to provide a method for producing such organosilicon compounds.

Solution to Problem

The inventors have conducted extensive investigations in order to achieve these objects. As a result, they have discovered specific organosilicon compounds having on the molecule a hydrolyzable silyl group and a plurality of epoxy groups, and a method for producing such compounds. The inventors have also discovered that compositions containing such organosilicon compounds give cured products capable of exhibiting good hydrophobic properties, heat resistance, yellowing resistance and crack resistance, and therefore are suitable as coating compositions and adhesive compositions.

Accordingly, the invention provides:

1. An organosilicon compound having formula (1)

[Chem. 1]

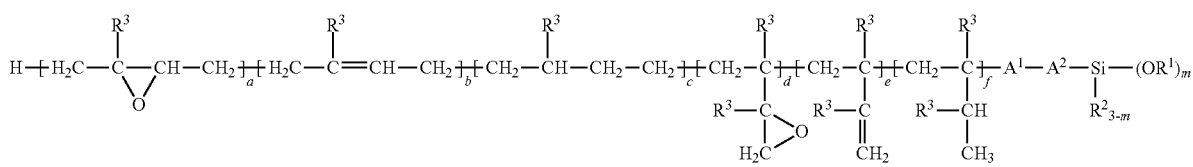

(1)

(wherein each $R^1$ is independently a substituted or unsubstituted alkyl group of 1 to 10 carbon atoms or a substituted or unsubstituted aryl group of 6 to 10 carbon atoms, each $R^2$ is independently a substituted or unsubstituted alkyl group of 1 to 10 carbon atoms or a substituted or unsubstituted aryl group of 6 to 10 carbon atoms, each $R^3$ is independently a hydrogen atom or a methyl group, $A^1$ is a single bond, O, S, NH or a heteroatom-containing divalent linkage, $A^2$ is a single bond or a substituted or unsubstituted divalent hydrocarbon group of 1 to 20 carbon atoms which may contain a heteroatom, the subscripts a and c are each independently a number larger than 0, the subscripts b, d, e and f are each independently a number of 0 or more, and m is an integer from 1 to 3, with the proviso that individual recurring units are arranged in any order);

2. The organosilicon compound of 1 above, wherein $A^1$-$A^2$ have formula (2) or (3);

[Chem. 2]

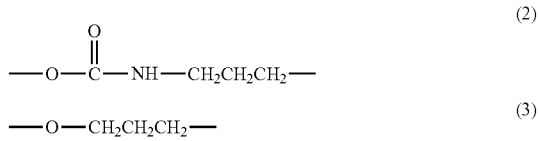

3. A method for producing the organosilicon compound of 1 or 2 above, comprising the step of reacting a hydroxyl group-containing compound of formula (4)

[Chem. 3]

(4)

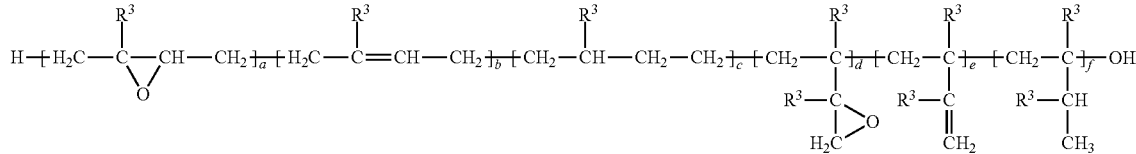

(wherein $R^3$ and the subscripts a to f are as defined above, with the proviso that individual recurring units are arranged in any order) with an isocyanate group and alkoxysilyl group-containing compound of formula (5)

[Chem. 4]

(5)

(wherein $R^1$, $R^2$, $A^2$ and m are as defined above);
4. A method for producing the organosilicon compound of 1 or 2 above, comprising the steps of reacting a hydroxyl group-containing compound of formula (4)

[Chem. 5]

(4)

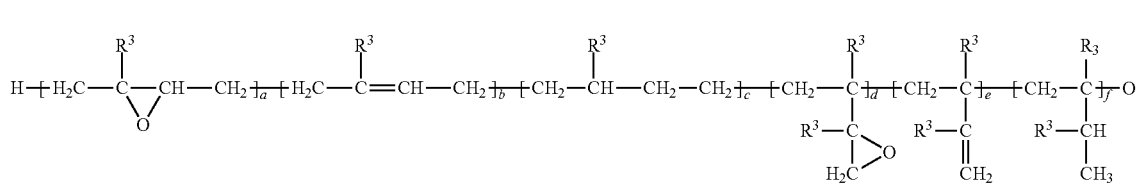

(wherein $R^3$ and the subscripts a to f are as defined above, with the proviso that individual recurring units are arranged in any order) with a compound having both a functional group capable of reacting with the hydroxyl group and an alkenyl group to form an alkenyl compound; and subjecting the alkenyl compound and a silane compound of formula (6)

[Chem. 6]

(6)

(wherein $R^1$, $R^2$ and m are as defined above) to a hydrosilylation reaction in the presence of a platinum compound-containing catalyst;
5. A coating composition comprising the organosilicon compound of claim 1 or 2 above;
6. An adhesive composition comprising the organosilicon compound of 1 or 2 above;
7. A cured article having a covering layer obtained by curing the coating composition of 5 above; and
8. A cured article having a bonding layer obtained by curing the adhesive composition of 6 above.

Advantageous Effects of Invention

The organosilicon compound of the invention has a plurality of epoxy groups per hydrolyzable silyl group in the molecule and, compared with conventional epoxy-type silane coupling agents, has an increased number of reactive sites with organic resins, resulting in a greater bonding strength with organic resins. Therefore, when used to cover and treat various types of inorganic fillers such as glass fibers and silica, or ceramic and metallic substrates, the performance is greatly enhanced compared with conventional epoxy-type silane coupling agents having a 1:1 ratio of epoxy groups to silyl groups in the molecule.

Cured products obtained from compositions containing the organosilicon compound of the invention have excellent hydrophobic properties, heat resistance, yellowing resistance and crack resistance.

Compositions which contain the organosilicon compound of the invention and have such properties can be advantageously used as coating compositions and adhesive compositions.

DESCRIPTION OF EMBODIMENTS

The invention is described in detail below.

The organosilicon compound of the invention has formula (1). In formula (1) and subsequently described formula (4), individual recurring units are arranged in any order.

[Chem. 7]

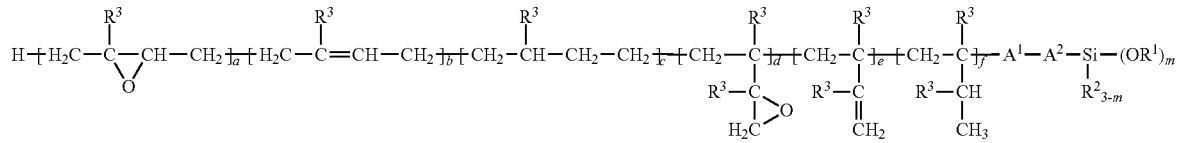

(1)

Here, each $R^1$ is independently a substituted or unsubstituted alkyl group of 1 to 10 carbon atoms or a substituted or unsubstituted aryl group of 6 to 10 carbon atoms; each $R^2$ is independently a substituted or unsubstituted alkyl group of 1 to 10 carbon atoms or a substituted or unsubstituted aryl group of 6 to 10 carbon atoms; each $R^3$ is independently a hydrogen atom or a methyl group; $A^1$ is a single bond, O, S, NH or a heteroatom-containing divalent linkage; $A^2$ is a single bond or a substituted or unsubstituted divalent hydrocarbon group of 1 to 20 carbon atoms which may contain a heteroatom; the subscripts a and c are each independently a number larger than 0; the subscripts b, d, e, f are each independently a number of 0 or more; and m is an integer from 1 to 3. As used herein, "single bond" refers to a morphology in which the groups on either side are directly bonded to each other; thus, when $A^2$ is a single bond, the morphology is one where $A^1$ and Si are directly bonded to each other.

The alkyl group of 1 to 10 carbon atoms may be linear, cyclic or branched. Specific examples include linear or branched alkyl groups such as methyl, ethyl, n-propyl, i-propyl, n-butyl, s-butyl, t-butyl, n-pentyl, n-hexyl, n-heptyl, n-octyl, n-nonyl and n-decyl groups; and cycloalkyl groups such as cyclopropyl, cyclobutyl, cyclopentyl, cyclohexyl, cycloheptyl and cyclooctyl groups.

Examples of aryl groups of 6 to 10 carbon atoms include phenyl, α-naphthyl and β-naphthyl groups.

Some or all hydrogen atoms in each of these groups may be substituted with, for example, alkyl groups of 1 to 10 carbon atoms, halogen atoms such as F, Cl and Br, or cyano groups. Specific examples of such groups include 3-chloropropyl, 3,3,3-trifluoropropyl, 2-cyanoethyl, tolyl and xylyl groups.

Of these, from the standpoint of hydrolyzability, $R^1$ is preferably a linear alkyl group of 1 to 5 carbon atoms, more preferably a methyl or ethyl group, and even more preferably an ethyl group.

$R^2$ is preferably a linear alkyl group, more preferably a methyl or ethyl group, and even more preferably a methyl group.

The subscript m is an integer from 1 to 3. From the standpoint of hydrolyzability, it is preferably 2 or 3, and more preferably 3.

The $R^3$ groups may be all hydrogen atoms, may be all methyl groups, or hydrogen atoms and methyl groups may both be included in any ratio.

Specific examples of the heteroatom-containing divalent linkage of $A^1$ above include the sulfonyl bond (—S(=O)$_2$—), phosphinyl bond (—P(=O)OH—), oxo bond (—C(=O)—), thiooxo bond (—C(=S)—), ester bond (—C(=O)O—), thioester bond (—C(=O)S—), thionoester bond (—C(=S)O—), dithioester bond (—C(=S)S—), carbonate bond (—OC(=O)O—), thiocarbonate bond (—OC(=S)O—), amide bond (—C(=O)NH—), thioamide bond (—C(=S)NH—), urethane bond (—OC(=O)NH—), thiourethane bond (—SC(=O)NH—), thionourethane bond (—OC(=S)NH—), dithiourethane bond (—SC(=S)NH—), urea bond (—NHC(=O)NH—) and thiourea bond (—NHC(=S)NH—).

$A^1$ is preferably O (ether bond) or a urethane bond (—OC(=O)NH—).

Specific examples of the divalent hydrocarbon group of 1 to 20 carbon atoms represented by $A^2$ which may have a heteroatom include alkylene groups such as methylene, ethylene, trimethylene, propylene, isopropylene, tetramethylene, isobutylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene and eicosadecylene groups; cycloalkylene groups such as cyclopentylene and cyclohexylene groups; and arylene groups such as phenylene, α-naphthalene and β-naphthalene groups.

These groups may include heteroatoms such as O, S or NH in the molecular chain, or may include the above divalent linkages. Also, some or all of the hydrogen atoms may be substituted with, for example, alkyl groups of 1 to 10 carbon atoms, halogen atoms such as F, Cl and Br, or cyano groups. Specific examples of such groups include tolylene and xylylene groups.

Of these, trimethylene and octamethylene groups are preferred; a trimethylene group is more preferred.

Therefore, suitable -$A^1$-$A^2$- groups are the trimethylene group having a urethane bond (—OC(=O)NH—) of formula (2) and the trimethylene group having an ether bond (—O—) of formula (3).

[Chem. 8]

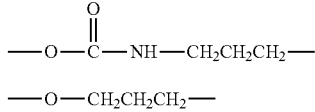

The weight-average molecular weight of the organosilicon compound of formula (1) above is not particularly limited. However, to set properties such as the viscosity of composition containing this compound within suitable ranges and thereby enhance the workability, and moreover to impart the resulting cured product with satisfactory hydrophobic properties, heat resistance and crack resistance, the weight-average molecular weight is preferably from 1,000 to 100,000, more preferably from 5,000 to 70,000, and even more preferably from 10,000 to 50,000. The weight-average molecular weight in this invention is a polystyrene-equivalent value obtained by gel permeation chromatography (GPC).

To increase the number of reactive sites with organic resins and thereby further elevate the bonding strength with organic resins, the epoxy equivalent weight is preferably from 100 to 10,000 g/mol, more preferably from 300 to 5,000 g/mol, even more preferably from 400 to 3,500 g/mol, and still more preferably from 500 to 3,000 g/mol.

Of the organosilicon compounds of formula (1), ones in which $A^1$ is a urethane bond can be obtained by reacting a compound of formula (4) having an epoxy group and a hydroxyl group on the molecule with an isocyanate group and alkoxysilyl group-containing compound of formula (5) (referred to below as "isocyanate silane").

More specifically, a reaction is carried out that forms a urethane bond between the hydroxyl group of the compound of formula (4) and the isocyanate group of the isocyanate silane.

[Chem. 9]

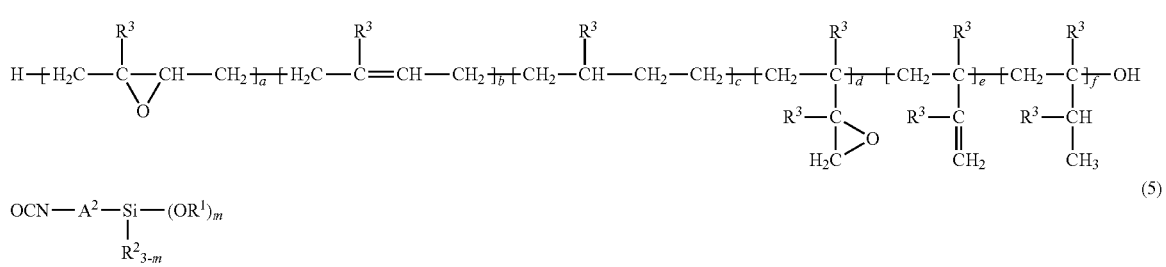

In these formulas, $R^1$, $R^2$, $R^3$, $A^2$, the subscripts a to f, and m are as defined above.

In the compound of formula (4) having an epoxy group and a hydroxyl group on the molecule, the molar ratio between the epoxy groups and the hydroxyl groups (number of moles of epoxy groups/number of moles of hydroxyl groups) is preferably from 1 to 100, more preferably from 2 to 50, and even more preferably from 3 to 20.

The epoxy equivalent weight, taking into account the ease of production and the properties of the resulting organosilicon compound, is preferably from 80 to 10,000 g/mol, more preferably from 200 to 5,000 g/mol, and even more preferably from 400 to 3,500 g/mol.

A commercial product may be used as the compound of formula (4). For example, L-207 available from Kuraray Co., Ltd. (an end-epoxidized hydrogenated butadiene-isoprene copolymer; identical to KRATON LIQUID™ Polymers (KLP) L-207 from Kraton Polymers Japan Ltd.) may be used.

Specific examples of the isocyanate silane include 3-isocyanatopropyltrimethoxysilane, 3-isocyanatopropylmethyldimethoxysilane, 3-isocyanatopropyldimethylmethoxysilane, 3-isocyanatopropyltriethoxysilane, 3-isocyanatopropylmethyldiethoxysilane and 3-isocyanatopropyldimethylethoxysilane.

Of these, from the standpoint of hydrolyzability, 3-isocyanatopropyltriethoxysilane and 3-isocyanatopropyltrimethoxysilane are preferred; 3-isocyanatopropyltrimethoxysilane is more preferred.

With regard to the reaction ratio between the compound of formula (4) having an epoxy group and a hydroxyl group on the molecule and the isocyanate silane, from the standpoint of suppressing by-products at the time of the urethane formation reaction and also increasing the shelf stability and properties of the resulting organosilicon compound, the ratio of isocyanate groups on the isocyanate silane per mole of hydroxyl groups in the compound of formula (4) is preferably from 0.01 to 1.2 moles, more preferably from 0.1 to 1.1 moles, and even more preferably from 0.5 to 1 mole.

A catalyst may be used in the urethane forming reaction to increase the reaction rate.

The catalyst may be suitably selected from among those which are commonly used in urethane-forming reactions. Specific examples include dibutyltin oxide, dioctyltin oxide, tin(II) bis(2-ethylhexanoate), dibutyltin dilaurate and dioctyltin dilaurate.

The amount of catalyst used, which may be the catalytic amount, is generally from 0.001 to 1 wt % based on the combined amount of the compound of formula (4) and the isocyanate silane.

In addition, a solvent which does not react with the starting materials that are used may be employed in the urethane-forming reaction.

Specific examples include hydrocarbon solvents such as pentane, hexane, heptane, octane, decane and cyclohexane; aromatic solvents such as benzene, toluene and xylene; ketone solvents such as acetone, methyl ethyl ketone and methyl isobutyl ketone; amide solvents such as formamide, N,N-dimethylformamide, pyrrolidone and n-methylpyrrolidone; ester solvents such as ethyl acetate, butyl acetate, γ-butyrolactone and propylene glycol 1-monomethyl ether 2-acetate; and ether solvents such as diethyl ether, dibutyl ether, cyclopentyl methyl ether, tetrahydrofuran and 1,4-dioxane. These may be used singly or two or more may be used in combination.

The reaction temperature at the time of the urethane-forming reaction is not particularly limited. However, to obtain a suitable reaction rate and suppress side reactions such as allophanate formation, the temperature is preferably from 25 to 90° C., and more preferably from 40 to 80° C.

The reaction time, although not particularly limited, is typically from 10 minutes to 24 hours.

Of the organosilicon compounds having formula (1), ones in which $A^1$ is an ether bond can be obtained by, as the first step, reacting a compound of formula (4) having an epoxy group and a hydroxyl group on the molecule with a compound having a functional group that can react with this hydroxyl group and an alkenyl group to form an alkenyl compound; and, as the second step, reacting the alkenyl compound obtained in the first step with a silane compound of formula (6).

More specifically, in the first step, the functional group capable of reacting with a hydroxyl group is reacted with the hydroxyl group, thereby coupling the compound of formula (4) and the compound having an alkenyl group via an ether bond. In the second step, the alkenyl group obtained in the first step and the silane compound of formula (6) are subjected to hydrosilylation in the presence of a platinum compound-containing catalyst, thereby adding a hydrosilyl group to the alkenyl group and forming a carbon-silicon bond.

[Chem. 10]

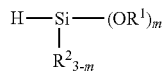

(6)

In the formula, $R^1$, $R^2$ and m are as defined above.

The functional group in the compound used in Step 1 having both a functional group that is capable of reacting with a hydroxyl group and an alkenyl group is not particularly limited, provided it is a functional group that reacts selectively with hydroxyl groups and does not react with epoxy groups. Examples include halogen atoms and the methanesulfonate, trifluoromethanesulfonate and p-toluenesulfonate groups. A halogen atom is preferred; chlorine, bromine and iodine atoms are more preferred.

Specific examples of compounds having a halogen atom and an alkenyl group (referred to below as "halogenated alkenyl compounds") include chlorinated alkenyl compounds such as allyl chloride, methallyl chloride, butenyl chloride, pentenyl chloride, hexenyl chloride, heptenyl chloride, octenyl chloride and nonenyl chloride; brominated alkenyl compounds such as allyl bromide, methallyl bromide, butenyl bromide, pentenyl bromide, hexenyl bromide, heptenyl bromide, octenyl bromide and nonenyl bromide; and iodinated alkenyl compounds such as allyl iodide, methallyl iodide, butenyl iodide, pentenyl iodide, hexenyl iodide, heptenyl iodide, octenyl iodide and nonenyl iodide.

Of these, from the standpoint of reactivity and availability, allyl chloride, hexenyl chloride, octenyl chloride, allyl bromide and allyl iodide are preferred; allyl chloride, octenyl chloride and allyl bromide are more preferred; and allyl bromide is even more preferred.

The Step 1 reaction may be carried out by an ordinary method known to the art. For example, use can be made of an asymmetric ether synthesis process (Williamson synthesis, Williamson ether synthesis) involving a nucleophilic substitution reaction between a hydroxyl group and a halogenated alkenyl compound in the presence of a basic compound.

In this case, the reaction ratio between the compound of formula (4) and the halogenated alkenyl compound is not particularly limited. However, to minimize the amount of unreacted starting materials and increase the shelf stability and properties of the resulting organosilicon compound, the ratio of halogen atoms on the halogenated alkenyl compound per mole of hydroxyl groups on the compound of formula (4) is preferably from 1 to 20 moles, more preferably from 1 to 10 moles, and even more preferably from 2 to 5 moles.

Various types of basic compounds ordinarily used in Williamson synthesis may be used as the basic compound. Any such compound that does not react with the epoxy group on the compound of formula (4) may be used.

Specific examples include alkali metals such as metallic sodium and metallic lithium; alkaline earth metals such as metallic calcium; alkali metal hydrides such as sodium hydride, lithium hydride, potassium hydride and cesium hydride; alkaline earth metal hydrides such as calcium hydride; alkali metal hydroxides such as lithium hydroxide, sodium hydroxide, potassium hydroxide and cesium hydroxide, as well as aqueous solutions thereof; alkaline earth metal hydroxides such as barium hydroxide and calcium hydroxide, as well as aqueous solutions thereof; alkali metal and alkaline earth metal alkoxides, such as potassium tert-butoxide and sodium tert-butoxide; alkali metal and alkaline earth metal carbonates, such as potassium carbonate, sodium carbonate and calcium carbonate; alkali metal and alkaline earth metal bicarbonates, such as sodium bicarbonate and potassium bicarbonate; and tertiary amines, such as triethylamine, tributylamine, N,N-diisopropylethylamine, tetramethylethylenediamine, pyridine and N,N-dimethyl-4-aminopyridine.

Of these, from the standpoint of the reaction efficiency, alkali metal and alkaline earth metal hydroxides such as lithium hydroxide, sodium hydroxide, potassium hydroxide, cesium hydroxide, barium hydroxide and calcium hydroxide, as well as aqueous solutions thereof, are preferred. An aqueous solution of sodium hydroxide is more preferred.

Although the amount of the basic compound used is not particularly limited, to have the etherification reaction sufficiently proceed and prevent the starting materials from remaining behind, and also to prevent an excessive amount of the basic compound from remaining and thereby increase the shelf stability and properties of the organosilicon compound, the amount of basic compound used per mole of hydroxyl groups on the resulting compound of formula (4) is preferably from 0.5 to 20 moles, more preferably from 1 to 10 moles, and even more preferably from 2 to 8 moles.

In the above etherification reaction, use may be made of a solvent that does not react with the starting materials that are employed.

Specific examples include water; hydrocarbon solvents such as pentane, hexane, heptane, octane, decane and cyclohexane; aromatic solvents such as benzene, toluene and xylene; amides such as formamide, N,N-dimethylformamide, pyrrolidone and N-methylpyrrolidone; ether solvents such as diethyl ether, dibutyl ether, cyclopentyl methyl ether, tetrahydrofuran and 1,4-dioxane; and nitrile solvents such as acetonitrile. These may be used singly or two or more may be used in combination.

Of these, from the standpoint of reaction efficiency, water, toluene, xylene, dimethylformamide, cyclopentyl methyl ether and tetrahydrofuran are preferred; mixed solvents of water and toluene, and mixed solvents of water and xylene are more preferred.

The reaction temperature during the etherification reaction is not particularly limited. However, to obtain a suitable reaction rate and yet keep the halogenated alkenyl compound from vaporizing, the temperature is preferably from 25 to 90° C., more preferably from 40 to 80° C., and even more preferably from 50 to 70° C.

The etherification reaction is generally carried out at atmospheric pressure, although it may be carried out under applied pressure so as to, for example, keep the halogenated alkenyl compound from vaporizing and increase the reaction rate.

The reaction time, although not particularly limited, is generally from 10 minutes to 24 hours.

A catalyst may be used in the etherification reaction to increase the reaction rate.

The catalyst, which is one that does not react with the epoxy groups of the compound of formula (4), may be suitably selected from among catalysts commonly used in the Williamson synthesis.

Specific examples include crown ethers such as 12-crown-4,15-crown-5, 18-crown-6 and dibenzo-18-crown-6; quaternary ammonium salts such as tetrabutylammonium chloride, tetrabutylammonium bromide, tetrabutylammonium iodide and tetrabutylammonium hydrogensulfate; and alkali metal halides such as potassium iodide and sodium iodide. These may be used singly or two or more may be used in combination.

Of these, from the standpoint of reactivity and availability, 18-crown-6, tetrabutylammonium bromide, tetrabutylammonium iodide, tetrabutylammonium hydrogensulfate and potassium iodide are preferred; tetrabutylammonium iodide, tetrabutylammonium hydrogensulfate and potassium iodide are more preferred; tetrabutylammonium hydrogensulfate is even more preferred.

The catalyst is able to increase the reaction rate by acting as a phase transfer catalyst or activating the halogenated alkenyl compound.

The amount of catalyst used, which may be the catalytic amount, is preferably from 0.001 to 10 wt %, and more preferably from 0.01 to 1 wt %, based on the combined amount of the compound of formula (4) and the halogenated alkenyl compound.

In Step 2, specific examples of the silane compound of formula (6) that may be used in the reaction with the alkenyl compound obtained in Step 1 include trimethoxysilane, methyldimethoxysilane, dimethylmethoxysilane, triethoxysilane, methyldiethoxysilane and dimethylethoxysilane. From the standpoint of hydrolyzability, trimethoxysilane and triethoxysilane are preferred; trimethoxysilane is more preferred.

The platinum compound-containing catalyst that may be used in the Step 2 hydrosilylation is not particularly limited. Specific examples include chloroplatinic acid, alcohol solutions of chloroplatinic acid, toluene or xylene solutions of platinum-1,3-divinyl-1,1,3,3-tetramethyldisiloxane complex, tetrakistriphenylphosphine platinum, dichlorobistriphenylphosphine platinum, dichlorobisacetonitrile platinum, dichlorobisbenzonitrile platinum, dichlorocyclooctadiene platinum, and supported catalysts such as platinum on carbon, platinum on alumina and platinum on silica.

Of these, from the standpoint of selectivity, a platinum(0) complex is preferred; a toluene or xylene solution of platinum-1,3-divinyl-1,1,3,3-tetramethyldisiloxane complex is more preferred.

The amount of platinum compound-containing catalyst used is not particularly limited. However, in terms of reactivity, productivity and the like, the amount is such that the quantity of platinum atoms included per mole of the silane compound of formula (6) is preferably from $1 \times 10^{-7}$ to $1 \times 10^{-2}$ mole, and more preferably from $1 \times 10^{-7}$ to $1 \times 10^{-3}$ mole.

A co-catalyst for increasing the hydrosilylation reactivity may be used. The co-catalyst may be one that is commonly used in hydrosilylation. In this invention, ammonium salts of inorganic acids, acid amide compounds and carboxylic acids are preferred.

Specific examples of ammonium salts of inorganic acids include ammonium chloride, ammonium sulfate, ammonium sulfamate, ammonium nitrate, ammonium dihydrogen phosphate, diammonium hydrogenphosphate, triammonium phosphate, ammonium hypophosphite, ammonium carbonate, ammonium bicarbonate, ammonium sulfate, ammonium borate and ammonium borofluoride. Of these, an ammonium salt of an inorganic acid having a pKa of at least 2 is preferred; ammonium carbonate and ammonium bicarbonate are more preferred.

Specific examples of acid amide compounds include formamide, acetamide, N-methylacetamide, N,N-dimethylacetamide, propionamide, acrylamide, malonamide, succinamide, maleamide, fumaramide, benzamide, phthalamide, palmitamide and stearamide.

Specific examples of carboxylic acids include formic acid, acetic acid, propionic acid, butyric acid, methoxybutyric acid, pentanoic acid, caproic acid, heptanoic acid, octanoic acid, lactic acid and glycolic acid. Of these, formic acid, acetic acid and lactic acid are preferred; acetic acid is more preferred.

The amount of co-catalyst used is not particularly limited. However, from the standpoint of reactivity, selectivity, cost and the like, the amount per mole of the silane compound of formula (6) is preferably from $1 \times 10^{-5}$ to $1 \times 10^{-1}$ mole, and more preferably from $1 \times 10^{-4}$ to $5 \times 10^{-1}$ mole.

The hydrosilylation reaction proceeds even in the absence of a solvent, although a solvent may be used.

Specific examples of solvents that may be used include hydrocarbon solvents such as pentane, hexane, cyclohexane, heptane, isooctane, benzene, toluene and xylene; ether solvents such as diethyl ether, tetrahydrofuran and dioxane; ester solvents such as ethyl acetate and butyl acetate; aprotic polar solvents such as N,N-dimethylformamide; and chlorinated hydrocarbon solvents such as dichloromethane and chloroform. These solvents may be used singly or two or more may be used in admixture.

The reaction temperature in the hydrosilylation reaction is not particularly limited. The reaction may be carried out at from 0° C. up to under heating, although the temperature is preferably from 0 to 200° C.

Carrying out the reaction under heating is preferred for obtaining a suitable reaction rate. From this standpoint, the reaction temperature is more preferably from 40 to 110° C., and even more preferably from 40 to 90° C.

The reaction time also is not particularly limited, and is generally from about 1 hour to about 60 hours, preferably from 1 to 30 hours, and more preferably from 1 to 20 hours.

The coating composition and adhesive composition of the invention (sometimes referred to collectively below as the "compositions") include an organosilicon compound of formula (1).

The organosilicon compound of formula (1) of the invention imparts hydrophobic properties to cured articles obtained by coating treatment or adhesion treatment using a composition containing the compound. Also, in the case of adhesive compositions, it acts as an adhesion promoter and, moreover, owing to the structure of this organosilicon compound, increases the heat resistance, yellowing resistance and crack resistance of the cured product compared with conventional organosilicon compounds.

The composition of the invention may include a curing catalyst for efficiently curing the composition.

The curing catalyst is not particularly limited, provided it is a curing catalyst that can be used to cure ordinary moisture condensation-curing compositions. Specific examples include alkyltin ester compounds such as dibutyltin diacetate, dibutyltin dilaurate, dioctyltin dilaurate, dibutyltin dioctoate and dioctyltin dioctoate; titanate esters, titanium chelate compounds and partial hydrolyzates of these, such as tetraisopropoxytitanium, tetra-n-butoxytitanium, tetrakis(2-ethylhexoxy)titanium, dipropoxybis(acetylacetonato)titanium and titanium isopropoxy octylene glycol; organometallic compounds such as zinc naphthenate, zinc stearate, zinc 2-ethyloctoate, iron 2-ethylhexoate, cobalt 2-ethylhexoate, manganese 2-ethylhexoate, cobalt naphthenate, aluminum trihydroxide, aluminum alcoholate, aluminum acylate, salts of aluminum acylate, aluminosiloxy compounds and aluminum chelate compounds; aminoalkyl group-substituted alkoxysilanes such as 3-aminopropyltriethoxysilane and N-β(aminoethyl)-γ-aminopropyltrimethoxysilane; amino compounds and salts thereof, such as hexylamine and dodecylamine phosphate; quaternary ammonium salts such as benzyltriethylammonium acetate; lower fatty acids salts of alkali metals, such as potassium acetate, sodium acetate and lithium oxalate; dialkylhydroxylamines such as dimethylhydroxylamine and diethylhydroxylamine; guanidyl group-containing silanes and siloxanes, such as tetramethylguanidylpropyltrimethoxysilane, tetramethylguanidylpropylmethyldimethoxysilane and tetramethylguanidylpropyltris(trimethylsiloxy)silane; and phosphazene base-containing silanes and siloxanes, such as N,N,N',N',N'',N''-hexamethyl-N'''-[3-(trimethoxysilyl)propyl]-phosphorimidic triamide. These may be used singly, or two or more may be used in combination.

Of these, tetraisopropoxytitanium, tetra-n-butoxytitanium and partial hydrolyzates thereof are preferred for their better reactivity; tetra-n-butoxytitanium is more preferred.

The amount of curing catalyst added is not particularly limited. However, to adjust the curing rate in a suitable range and enhance the workability, the amount of addition per 100 parts by weight of the organosilicon compound of formula (1) is preferably from 0.01 to 15 parts by weight, and more preferably from 0.1 to 5 parts by weight.

In addition, the composition of the invention may include a solvent.

The solvent is not particularly limited, provided that it has the ability to dissolve the organosilicon compound of formula (1) that is the chief ingredient. From the standpoint of properties such as solubility and volatility, aromatic solvents such as toluene and xylene, ketone solvents such as methyl ethyl ketone and methyl isobutyl ketone, and ether solvents such as tetrahydrofuran are preferred. Of these, toluene and tetrahydrofuran are more preferred.

The amount of solvent added per 100 parts by weight of the organosilicon compound of formula (1) is preferably from 10 to 20,000 parts by weight, and more preferably from 100 to 10,000 parts by weight.

A coated solid substrate that is a cured article can be obtained by applying the coating composition of the invention to the surface of a solid substrate and curing to form a coating layer. A bonded laminate that is a cured article can be obtained by applying the adhesive composition of the invention to the surface of a solid substrate, laminating another solid substrate thereon, and then curing the composition to form a bonding layer.

Specific examples of solid substrates include the following: epoxy resins, phenolic resins, polyimide resins, unsaturated polyester resins, polycarbonate resins such as polycarbonates and polycarbonate blends, acrylic resins such as poly(methyl methacrylate), polyester resins such as poly(ethylene terephthalate) and poly(butylene terephthalate), polyamide resins, acrylonitrile-styrene copolymer resins, styrene-acrylonitrile-butadiene copolymer resins, polyvinyl chloride resins, polystyrene resins, blends of polystyrene and polyphenylene ether, cellulose acetate butyrate, polyethylene resins and other organic resin substrates; metal substrates; paint-coated surfaces; glass; ceramic; concrete; slate boards; textiles; inorganic fillers such as (hollow) silica, titania, zirconia and alumina; and glass fiber products such as glass fibers, glass cloth, glass tape, glass mats and glass paper. The substrate material and shape are not particularly limited.

When the composition of the invention comes into contact with moisture in the atmosphere, a hydrolytic condensation reaction on the organosilicon compound of formula (1) proceeds. The moisture level in the atmosphere may be anywhere from 10 to 100% relative humidity; because hydrolysis generally proceeds more rapidly at a higher humidity, where desired, moisture may be added to the atmosphere.

The curing reaction temperature and time may be suitably varied according to such factors as the substrate used, the moisture concentration, the catalyst concentration and the type of hydrolyzable group. Curing is generally carried out for a period of from about 5 minutes to about one week at a temperature that does not exceed the heat-resistant temperature of the substrate used. However, curing is preferably carried for a period of from 10 minutes to 2 hours with heating within a temperature range that does not exceed the heat-resistant temperature of the substrate. Curing is more preferably carried out at from 30° C. to 180° C. for a period of from 30 minutes to 2 hours.

EXAMPLES

The invention is illustrated more fully below by way of Working Examples and Comparative Examples, although the invention is not limited by these Examples.

In the Examples below, the viscosity is the value measured at 25° C. using a Brookfield rotational viscometer, and the molecular weight is the polystyrene-equivalent weight-average molecular weight obtained by measurement using gel permeation chromatography (GPC). The viscosity is the value at 25° C. measured using a rotational viscometer. The epoxy equivalent weight, which is expressed in units of g/mol, indicates the weight of epoxy compound having one mole of epoxy groups.

[1] Production of Organosilane Compound

[Working Example 1-1] Synthesis of Organosilicon Compound 1

A 300-mL separable flask equipped with a stirrer, a reflux condenser, a dropping funnel and a thermometer was charged with 200 g of an end-epoxidized hydrogenated butadiene-isoprene copolymer having an epoxy equivalent weight of 869 g/mol (L-207, from Kuraray Co., Ltd.) and 0.11 g of dioctyltin dilaurate, and heated to 80° C. To this was added dropwise 11.8 g of 3-isocyanatopropyltrimethoxysilane and the flask contents were stirred under heating at 80° C. for 2 hours. After subsequently confirming by IR spectroscopy that the absorption peak for isocyanate groups in the starting materials had completely vanished and the absorption peak for urethane linkages had formed instead, the reaction was brought to completion.

The reaction product was a clear light-yellow liquid that had a weight-average molecular weight of 13,750, a viscosity of 230,000 mPa·s, and an epoxy equivalent weight of 1,400 g/mol.

[Working Example 1-2] Synthesis of Organosilicon Compound 2

A 300-mL separable flask equipped with a stirrer, a reflux condenser, a dropping funnel and a thermometer was charged with 200 g of an end-epoxidized hydrogenated butadiene-isoprene copolymer having an epoxy equivalent weight of 869 g/mol (L-207, from Kuraray Co., Ltd.) and 0.11 g of dioctyltin dilaurate, and heated to 80° C. To this was added dropwise 14.2 g of 3-isocyanatopropyltriethoxysilane and the flask contents were stirred under heating at 80° C. for 2 hours. After subsequently confirming by IR spectroscopy that the absorption peak for isocyanate groups in the starting materials had completely vanished and the absorption peak for urethane linkages had formed instead, the reaction was brought to completion.

The reaction product was a clear light-yellow liquid that had a weight-average molecular weight of 13,000, a viscosity of 200,000 mPa·s, and an epoxy equivalent weight of 1,420 g/mol.

[Working Example 1-3] Synthesis of Organosilicon Compound 3

A 300-mL separable flask equipped with a stirrer, a reflux condenser, a dropping funnel and a thermometer was charged with 200 g of an end-epoxidized hydrogenated butadiene-isoprene copolymer having an epoxy equivalent weight of 869 g/mol (L-207, from Kuraray Co., Ltd.) and 0.11 g of dioctyltin oxide, and heated to 80° C. To this was added dropwise 11.8 g of 3-isocyanatopropyltrimethoxysilane and the flask contents were stirred under heating at 80° C. for 2 hours. After subsequently confirming by IR spectroscopy that the absorption peak for isocyanate groups in the starting materials had completely vanished and the absorption peak for urethane linkages had formed instead, the reaction was brought to completion.

The reaction product was a clear light-yellow liquid that had a weight-average molecular weight of 14,200, a viscosity of 250,000 mPa·s, and an epoxy equivalent weight of 1,380 g/mol.

[Working Example 1-4] Synthesis of Organosilicon Compound 4

A 300-mL separable flask equipped with a stirrer, a reflux condenser, a dropping funnel and a thermometer was charged with 200 g of an end-epoxidized hydrogenated butadiene-isoprene copolymer having an epoxy equivalent weight of 869 g/mol (L-207, from Kuraray Co., Ltd.), and heated to 80° C. To this was added dropwise 11.8 g of 3-isocyanatopropyltrimethoxysilane and the flask contents were stirred under heating at 80° C. for 6 hours. After subsequently confirming by IR spectroscopy that the absorption peak for isocyanate groups in the starting materials had completely vanished and the absorption peak for urethane linkages had formed instead, the reaction was brought to completion.

The reaction product was a clear light-yellow liquid that had a weight-average molecular weight of 15,700, a viscosity of 270,000 mPa·s, and an epoxy equivalent weight of 1,000 g/mol.

[Working Example 1-5] Synthesis of Organosilicon Compound 5

[First Step]
A 200-mL separable flask equipped with a stirrer, a reflux condenser, a dropping funnel and a thermometer was charged with 50 g of an end-epoxidized hydrogenated butadiene-isoprene copolymer having an epoxy equivalent weight of 869 g/mol (L-207, from Kuraray Co., Ltd.), 50 mL of toluene, 0.67 g of tetrabutylammonium hydrogensulfate and 37.6 g of a 30% aqueous solution of sodium hydroxide, and heated to 60° C. To this was added dropwise 17.1 g of allyl bromide and the flask contents were stirred under heating at 60° C. for 6 hours and then left at rest, allowing the mixture to separate into two layers. The aqueous layer was partitioned off, and the organic layer was washed with water to neutrality. In addition, the organic layer was concentrated in vacuo (80° C., 5 mmHg) to remove volatile ingredients and filtration was carried out, giving the corresponding alkenyl compound.

[Second Step]
A 300-mL separable flask equipped with a stirrer, a reflux condenser, a dropping funnel and a thermometer was charged with 100 g of the alkenyl compound obtained in the first step, 100 g of toluene, 0.19 g of a toluene solution of platinum-1,3-divinyl-1,1,3,3-tetramethyldisiloxane complex (amount in terms of platinum atoms per mole of trimethoxysilane, $5.0 \times 10^{-4}$ mole) and 0.003 g of acetic acid ($5.0 \times 10^{-2}$ mole per mole of trimethoxysilane), and 1.17 g of trimethoxysilane was added at an internal temperature of 75 to 85° C., following which the flask contents were stirred at 80° C. for 1 hour. After the completion of stirring, concentration in vacuo (80° C., 5 mmHg) and filtration were carried out, giving a clear light-yellow liquid having a viscosity of 150,000 mPa·s. The resulting product had a weight-average molecular weight of 10,870 and an epoxy equivalent weight of 1,380 g/mol.

[Working Example 1-6] Synthesis of Organosilicon Compound 6

[First Step]
A 200-mL separable flask equipped with a stirrer, a reflux condenser, a dropping funnel and a thermometer was charged with 50 g of an end-epoxidized hydrogenated butadiene-isoprene copolymer having an epoxy equivalent weight of 869 g/mol (L-207, from Kuraray Co., Ltd.), 50 mL of toluene, 0.61 g of tetrabutylammonium iodide and 37.6 g of a 30% aqueous solution of sodium hydroxide, and heated to 60° C. To this was added dropwise 10.8 g of allyl chloride and the flask contents were stirred under heating at 60° C. for 6 hours and then left at rest, allowing the mixture to separate into two layers. The aqueous layer was partitioned off, and the organic layer was washed with water to neutrality. In addition, the organic layer was concentrated in vacuo (80° C., 5 mmHg) to remove volatile ingredients and filtration was carried out, giving the corresponding alkenyl compound.

[Second Step]
A 300-mL separable flask equipped with a stirrer, a reflux condenser, a dropping funnel and a thermometer was charged with 100 g of the alkenyl compound obtained in the first step, 100 g of toluene, 0.19 g of a toluene solution of platinum-1,3-divinyl-1,1,3,3-tetramethyldisiloxane complex (amount in terms of platinum atoms per mole of triethoxysilane, $5.0 \times 10^{-4}$ mole) and 0.003 g of acetic acid ($5.0 \times 10^{-2}$ mole per mole of trimethoxysilane), and 1.57 g of triethoxysilane was added at an internal temperature of 75 to 85° C., following which the flask contents were stirred at 80° C. for 1 hour. After the completion of stirring, concentration in vacuo (80° C., 5 mmHg) and filtration were carried out, giving a clear light-yellow liquid having a viscosity of 160,000 mPa·s. The resulting product had a weight-average molecular weight of 11,000 and an epoxy equivalent weight of 1,400 g/mol.

[Working Example 1-7] Synthesis of Organosilicon Compound 7

[First Step]

A 200-mL separable flask equipped with a stirrer, a reflux condenser, a dropping funnel and a thermometer was charged with 50 g of an end-epoxidized hydrogenated butadiene-isoprene copolymer having an epoxy equivalent weight of 869 g/mol (L-207, from Kuraray Co., Ltd.), 50 mL of toluene, 0.57 g of potassium iodide and 37.6 g of a 30% aqueous solution of sodium hydroxide, and heated to 60° C. To this was added dropwise 6.9 g of octenyl chloride and the flask contents were stirred under heating at 80° C. for 6 hours and then left at rest, allowing the mixture to separate into two layers. The aqueous layer was partitioned off, and the organic layer was washed with water to neutrality. In addition, the organic layer was concentrated in vacuo (80° C., 5 mmHg) to remove volatile ingredients and filtration was carried out, giving the corresponding alkenyl compound.

[Second Step]

A 300-mL separable flask equipped with a stirrer, a reflux condenser, a dropping funnel and a thermometer was charged with 100 g of the alkenyl compound obtained in the first step, 100 g of toluene, 0.18 g of a toluene solution of platinum-1,3-divinyl-1,1,3,3-tetramethyldisiloxane complex (amount in terms of platinum atoms per mole of triethoxysilane, $5.0 \times 10^{-4}$ mole) and 0.003 g of acetic acid ($5.0 \times 10^{-2}$ mole per mole of trimethoxysilane), and 1.16 g of trimethoxysilane was added at an internal temperature of 75 to 85° C., following which the flask contents were stirred at 80° C. for 1 hour. After the completion of stirring, concentration in vacuo (80° C., 5 mmHg) and filtration were carried out, giving a clear light-yellow liquid having a viscosity of 180,000 mPa·s. The resulting product had a weight-average molecular weight of 10,970 and an epoxy equivalent weight of 1,450 g/mol.

[Comparative Example 1-1] Synthesis of Organosilicon Compound 8

A one-liter separable flask equipped with a stirrer, a reflux condenser, a dropping funnel and a thermometer was charged with 100 g of a polyglycerol polyglycidyl ether having an epoxy equivalent weight of 172 g/mol (Denacol EX-1610, from Nagase ChemteX Corporation) and heated to 80° C. To this was added dropwise 49.9 g of 3-isocyanatopropyltriethoxoysilane and the flask contents were stirred under heating at 80° C. for 4 hours. After subsequently confirming by IR spectroscopy that the absorption peak for isocyanate groups in the starting materials had completely vanished and the absorption peak for urethane linkages had formed instead, the reaction was brought to completion. The reaction product was a clear light-yellow liquid that had a weight-average molecular weight of 3,800, a viscosity of 1,421 mPa·s, and an epoxy equivalent weight of 261 g/mol.

[Comparative Example 1-2] Synthesis of Organosilicon Compound 9

A one-liter separable flask equipped with a stirrer, a reflux condenser, a dropping funnel and a thermometer was charged with 100 g of a sorbitol polyglycidyl ether having an epoxy equivalent weight of 220 g/mol (Denacol EX-610U, from Nagase ChemteX Corporation) and heated to 80° C. To this was added dropwise 39.8 g of 3-isocyanatopropyltriethoxoysilane and the flask contents were stirred under heating at 80° C. for 4 hours. After subsequently confirming by IR spectroscopy that the absorption peak for isocyanate groups in the starting materials had completely vanished and the absorption peak for urethane linkages had formed instead, the reaction was brought to completion. The reaction product was a cloudy light-yellow liquid that had a weight-average molecular weight of 3,600, a viscosity of 1,114 mPa·s, and an epoxy equivalent weight of 315 g/mol.

[Heat Resistance]

The loss of weight on heating was measured for each of the organosilicon compounds obtained in Working Examples 1-1 to 1-7 and Comparative Examples 1-1 and 1-2.

Measurement was carried out using a differential thermobalance (TG8120, from Rigaku Corporation) under the following conditions: measurement temperature, 25 to 500° C.; temperature rise rate, 10.0° C./min; measurement atmosphere, air; air flow rate, 100 mL/min. In the method of evaluation, $T_5$ represents the temperature when the weight has fallen by 5% of the total sample weight and $T_{10}$ represents the temperature when the weight has fallen by 10% of the total sample weight. The results are shown in Tables 1 and 2 below.

[2] Production of Coating Composition and Cured Film

Working Example 2-1

A coating composition was prepared by using a stirrer to uniformly mix together 100 parts by weight of Organosilicon Compound 1 obtained in Working Example 1-1, 1 part by weight of tetra-n-butoxytitanium as the curing catalyst and 100 parts by weight of tetrahydrofuran as the solvent.

The resulting coating composition was applied onto a glass plate using a No. 14 bar coater in 25° C., 50% RH air, after which it was dried and cured for four days in 25° C., 50% RH air, then dried and cured for 2 hours at 105° C. and additionally dried and cured for 2 hours at 150° C., giving a cured film.

Working Examples 2-2 to 2-7, and Comparative Examples 2-1 to 2-4

Aside from changing Organosilicon Compound 1 obtained in Working Example 2-1 to Organosilicon Compounds 2 to 9 obtained in Working Examples 1-2 to 1-7 and Comparative Examples 1-1 and 1-2, coating compositions and cured films were produced in the same way as in Working Example 2-1.

In addition, aside from changing Organosilicon Compound 1 to, respectively, γ-glycidoxypropyltrimethoxysilane (KBM-403, from Shin-Etsu Chemical Co., Ltd.) as Comparative Example 1-3 and glycidoxyoctyltrimethoxysilane (KBM-4803, from Shin-Etsu Chemical Co., Ltd.) as Comparative Example 1-4, coating compositions and cured films were produced in the same way as in Working Example 2-1.

The cured films produced in Working Examples 2-1 to 2-7 and Comparative Examples 2-1 to 2-4 were evaluated as described below. The results are presented in Tables 1 and 2.

[Water Contact Angle]

The water contact angle of the cured film was measured as a five-point average.

[Yellowing Resistance]

The degree of yellowing by the cured film was visually checked.

When yellowing was not observed, the yellowing resistance was rated as "◯" (Good); when distinct yellowing was observed, the yellowing resistance was rated as "×".

[Crack Resistance]

The cured film was checked for the presence or absence of cracks.

When no cracks whatsoever were observed, the crack resistance was rated as "◯" (Good); when a single crack was observed, the crack resistance was rated as "×". When two or more cracks were observed, the crack resistance was rated as "××".

TABLE 1

|  |  | Example | | | | | | |
| --- | --- | --- | --- | --- | --- | --- | --- | --- |
|  |  | 2-1 | 2-2 | 2-3 | 2-4 | 2-5 | 2-6 | 2-7 |
| Organosilicon compound |  | 1 | 2 | 3 | 4 | 5 | 6 | 7 |
| Water contact angle (°) |  | 114 | 116 | 115 | 116 | 115 | 115 | 116 |
| Heat resistance of organo- | $T_5$ | 266 | 260 | 265 | 264 | 268 | 263 | 255 |
| silicon compound (° C.) | $T_{10}$ | 342 | 335 | 340 | 338 | 345 | 342 | 320 |
| Yellowing resistance |  | ◯ | ◯ | ◯ | ◯ | ◯ | ◯ | ◯ |
| Crack resistance |  | ◯ | ◯ | ◯ | ◯ | ◯ | ◯ | ◯ |

TABLE 2

|  |  | Comparative Example | | | |
| --- | --- | --- | --- | --- | --- |
|  |  | 2-1 | 2-2 | 2-3 | 2-4 |
| Organosilicon compound |  | 8 | 9 | KBM-403 | KBM-4803 |
| Water contact angle (°) |  | 63 | 62 | 74 | 70 |
| Heat resistance of | $T_5$ | 200 | 148 | — | — |
| organosilicon compound | $T_{10}$ | 241 | 214 | — | — |
| (° C.) |  |  |  |  |  |
| Yellowing resistance |  | X | X | ◯ | ◯ |
| Crack resistance |  | X | X | XX | ◯ |

As is apparent from Tables 1 and 2, compared to the organosilicon compounds obtained in Comparative Examples 1-1 and 1-2, each of the organosilicon compounds obtained in Working Examples 1-1 to 1-7 had an excellent heat resistance.

It is also apparent that, compared with the cured films produced in Comparative Examples 2-1 to 2-4, each of the cured films produced in Working Examples 2-1 to 2-7 using Organosilicon Compounds 1 to 7 obtained in the respective Working Examples had excellent hydrophobic properties, yellowing resistance and crack resistance.

The invention claimed is:

1. An organosilicon compound having formula (1)

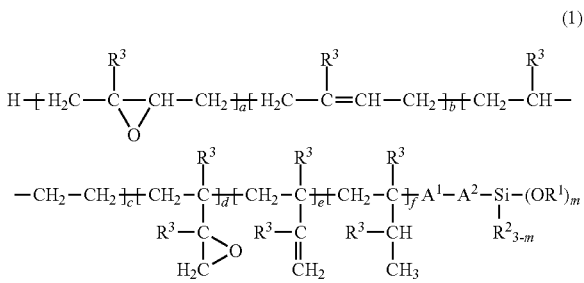

wherein each $R^1$ is independently a substituted or unsubstituted alkyl group of 1 to 10 carbon atoms or a substituted or unsubstituted aryl group of 6 to 10 carbon atoms, each $R^2$ is independently a substituted or unsubstituted alkyl group of 1 to 10 carbon atoms or a substituted or unsubstituted aryl group of 6 to 10 carbon atoms, each $R^3$ is independently a hydrogen atom or a methyl group, $A^1$ is a single bond, O, S, NH or a heteroatom-containing divalent linkage, $A^2$ is a single bond or a substituted or unsubstituted divalent hydrocarbon group of 1 to 20 carbon atoms which may contain a heteroatom, the subscripts a and c are each independently a number larger than 0, the subscripts b, d, e and f are each independently a number of 0 or more, and m is an integer from 1 to 3, with the proviso that individual recurring units are arranged in any order, and wherein $A^1$-$A^2$ has formula (2) or (3)

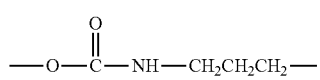

2. A method for producing the organosilicon compound of claim 1, comprising the step of reacting a hydroxyl group-containing compound of formula (4)

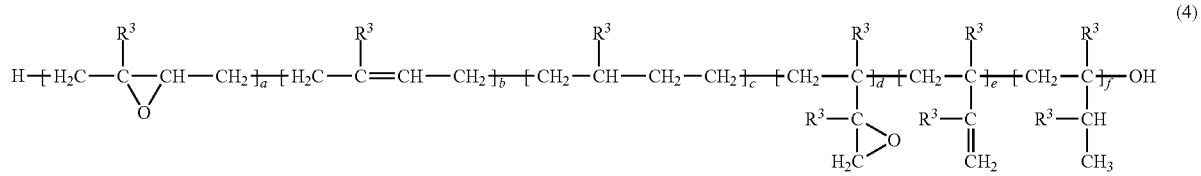

(4)

wherein R³ and the subscripts a to f are as defined above, with the proviso that individual recurring units are arranged in any order with an isocyanate group and alkoxys Hy' group-containing compound of formula (5)

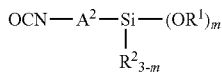

(5)

wherein R¹, R², A² and m are as defined above.

3. A method for producing the organosilicon compound of claim 1, comprising the steps of reacting a hydroxyl group-containing compound of formula (4)

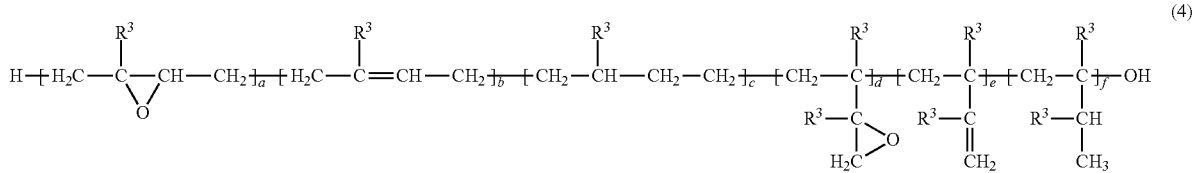

(4)

wherein R³ and the subscripts a to f are as defined above, with the proviso that individual recurring units are arranged in any order with a compound having both a functional group capable of reacting with the hydroxyl group and an alkenyl group to form an alkenyl compound; and subjecting the alkenyl compound and a silane compound of formula (6)

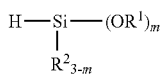

(6)

wherein R¹, R² and m are as defined above to a hydrosilylation reaction in the presence of a platinum compound-containing catalyst.

4. A coating composition comprising the organosilicon compound of claim 1.

5. An adhesive composition comprising the organosilicon compound of claim 1.

6. A cured article having a covering layer obtained by curing the coating composition of claim 4.

7. A cured article having a bonding layer obtained by curing the adhesive composition of claim 5.

* * * * *